US012582357B2

(12) United States Patent
Burkholz et al.

(10) Patent No.: US 12,582,357 B2
(45) Date of Patent: Mar. 24, 2026

(54) CLOSED SYSTEM FLEXIBLE VASCULAR ACCESS DEVICE SENSOR DEPLOYMENT SYSTEM

(71) Applicant: Becton, Dickinson and Company, Franklin Lakes, NJ (US)

(72) Inventors: Jonathan Karl Burkholz, Salt Lake City, UT (US); Megan S. Scherich, Salt Lake City, UT (US); Jack Balji, Mahwah, NJ (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 372 days.

(21) Appl. No.: 18/121,864

(22) Filed: Mar. 15, 2023

(65) Prior Publication Data

US 2023/0293109 A1 Sep. 21, 2023

Related U.S. Application Data

(60) Provisional application No. 63/321,950, filed on Mar. 21, 2022.

(51) Int. Cl.
| | |
|---|---|
| *A61B 5/00* | (2006.01) |
| *A61B 5/0205* | (2006.01) |
| *A61M 25/01* | (2006.01) |

(52) U.S. Cl.
CPC .......... *A61B 5/6852* (2013.01); *A61B 5/0205* (2013.01)

(58) Field of Classification Search
None
See application file for complete search history.

(56) References Cited

U.S. PATENT DOCUMENTS

| | | | |
|---|---|---|---|
| 2004/0102736 A1 | 5/2004 | Bierman | |
| 2009/0124880 A1* | 5/2009 | Smith | H01R 24/66 600/373 |
| 2011/0092955 A1* | 4/2011 | Purdy | A61B 5/6852 604/523 |
| 2013/0218032 A1* | 8/2013 | Belleville | A61B 5/0084 600/486 |
| 2014/0350416 A1 | 11/2014 | Balji et al. | |
| 2015/0196210 A1* | 7/2015 | McCaffrey | A61M 25/007 600/488 |
| 2015/0289929 A1 | 10/2015 | Toth et al. | |

(Continued)

FOREIGN PATENT DOCUMENTS

| | | |
|---|---|---|
| WO | 2015052235 A1 | 4/2015 |
| WO | 2021102467 A1 | 5/2021 |

*Primary Examiner* — Etsub D Berhanu
(74) *Attorney, Agent, or Firm* — The Webb Law Firm

(57) ABSTRACT

A sensor deployment system for a vascular access device includes: a primary lumen; a deployment connector configured to be connected to at least one of a luer connector; a needle-free connector; a catheter adapter, with the deployment connector attached to the primary lumen, an instrument with a sensor at least partially received within the primary lumen, with the instrument having a retracted position where a distal end of the instrument is positioned within the primary lumen or the deployment connector and an extended position where the distal end of the instrument extends beyond a distal end of the primary lumen and the deployment connector, and a communication device configured to transmit data from the sensor.

18 Claims, 18 Drawing Sheets

(56) References Cited

U.S. PATENT DOCUMENTS

| 2015/0305679 | A1 * | 10/2015 | Matsubara .......... A61M 1/3655 |
| | | | 600/485 |
| 2017/0043130 | A1 | 2/2017 | Jones et al. |
| 2017/0113000 | A1 * | 4/2017 | Tobescu ............ A61M 25/0017 |
| 2019/0070390 | A1 * | 3/2019 | Isaacson ............ A61B 5/14503 |
| 2019/0160275 | A1 | 5/2019 | Funk et al. |
| 2020/0023176 | A1 * | 1/2020 | Hu ........................ A61M 39/06 |
| 2020/0108237 | A1 * | 4/2020 | Ebrahimi .............. A61B 17/24 |
| 2021/0213268 | A1 | 7/2021 | Scherich et al. |
| 2021/0290126 | A1 | 9/2021 | Burkholz et al. |
| 2021/0299426 | A1 | 9/2021 | Scherich et al. |
| 2022/0386961 | A1 | 12/2022 | Mitchell et al. |

* cited by examiner

1

CLOSED SYSTEM FLEXIBLE VASCULAR ACCESS DEVICE SENSOR DEPLOYMENT SYSTEM

CROSS-REFERENCE TO RELATED APPLICATION

The present application claims priority to U.S. Provisional Application Ser. No. 63/321,950, entitled "Closed System Flexible Vascular Access Device Sensor Deployment System", filed Mar. 21, 2022, the entire disclosure of which is hereby incorporated by reference in its entirety.

BACKGROUND OF THE INVENTION

Field of the Invention

The present disclosure relates to a vascular access device sensor deployment system.

Description of Related Art

Catheters are frequently utilized to administer fluids into and out of the body. Patients in a variety of settings, including in hospitals and in home care, receive fluids, pharmaceuticals, and blood products via a vascular access device inserted into a patient's vascular system. Catheters of various types and sizes have been used extensively in a variety of procedures including, but not limited to, treating an infection, providing anesthesia or analgesia, providing nutritional support, treating cancerous growths, maintaining blood pressure and heart rhythm, and many other clinical uses. A common vascular access device is a plastic catheter that is inserted into a patient's vein. The catheter length may vary from a few centimeters for peripheral access to many centimeters for central access. The catheter is commonly incorporated into a catheter adapter to aid in the ease of use, accessibility and utility of the catheter. A catheter adapter may be adapted to house one end of the catheter such that one end of the catheter is supported by the catheter adapter and the body and tip of the catheter extends beyond a first end of the catheter adapter. A catheter adapter generally further includes a second end adapted to receive additional infusion components for use with the catheter. For example, the second end of a catheter adapter may include a set of threads for attaching an intravenous line or for coupling a syringe to the catheter adapter thereby providing access to the patient's vasculature via the attached catheter.

The catheter may be inserted transcutaneously. When inserted transcutaneously, the insertion of the catheter is commonly aided by an introducer needle. The introducer needle is commonly housed inside the lumen of the catheter such that the gauge of the needle approximates the inner diameter of the catheter. The needle is positioned within the catheter such that the needle tip extends beyond the tip of the catheter whereby the needle is used to penetrate the patient's vein and provide an opening for insertion of the catheter.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal, fluid infusion, or probe access.

SUMMARY OF THE INVENTION

In one aspect or embodiment, a sensor deployment system for a vascular access device includes a primary lumen, a deployment connector configured to be connected to at least one of a luer connector, a needle-free connector, and a catheter adapter, with the deployment connector attached to the primary lumen, an instrument at least partially received within the primary lumen, and a communication device. The instrument includes a sensor. The instrument has a retracted position where a distal end of the instrument is positioned within the primary lumen or the deployment connector and an extended position where the distal end of the instrument extends beyond a distal end of the primary lumen and the deployment connector. The communication device is configured to transmit data from the sensor.

The system may include an advancement member configured to be grasped by a healthcare technician, where movement of the advancement member moves the instrument between the retracted position and the extended position. The advancement member may be configured to move along an outer surface of the primary lumen, where the advancement member is entirely positioned outside of the primary lumen.

The system may include a catheter adapter including a catheter configured to be inserted into a patient's vasculature, with the deployment connector configured to be connected to the catheter adapter. The catheter adapter may include a side port and a joining connector in fluid communication with the side port, where the deployment connector is configured to be connected to the joining connector. The joining connector may include a needle-free connector, and the deployment connector may include a blunt cannula. The deployment connector may include an instrument seal.

The instrument may include a nitinol guidewire with an atraumatic tip. The system may include an electrical connector and wiring in communication with the sensor. The communication device may include a processor and a power source. The communication device may include a radio transceiver. The sensor may include at least one of a temperature sensor, a pressure sensor, a pH sensor, a flow rate sensor, and an optical sensor.

The system may include a stabilization member configured to be in contact with a patient's skin, where the communication device, the processor, and the power source are received by the stabilization member. The stabilization member may be positioned at a proximal end of the primary lumen. The communication device may be positioned at the distal end of the primary lumen. The deployment connector may include a threaded luer connector positioned at the distal end of the primary lumen.

The system may include a catheter adapter having a catheter configured to be inserted into a patient's vasculature, an extension set having a near patient access port, and an extension tube in fluid communication with the near patient access port, where the deployment connector is configured to be connected to the near patient access port. The extension set may include an extension set stabilization member configured to contact a patient's skin. The system may include a stabilization member configured to be in contact with a patient's skin, with the stabilization member positioned at a proximal end of the primary lumen, where the communication device includes a processor and a power source, and where the communication device is received by the stabilization member. The communication device may include a processor and a power source, where the communication device is positioned at a proximal end of the primary lumen.

In a further aspect or embodiment, a method of using the sensor deployment system of any of the aspects or embodiments discussed above includes: connecting the deployment connector to a catheter adapter having a catheter; advancing the instrument from the retracted position to the extended position such that the distal end of the instrument extends beyond a distal end of the catheter; collecting data from the sensor; and transmitting the data to an external device using the communication device.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION OF THE INVENTION

Figure 1:
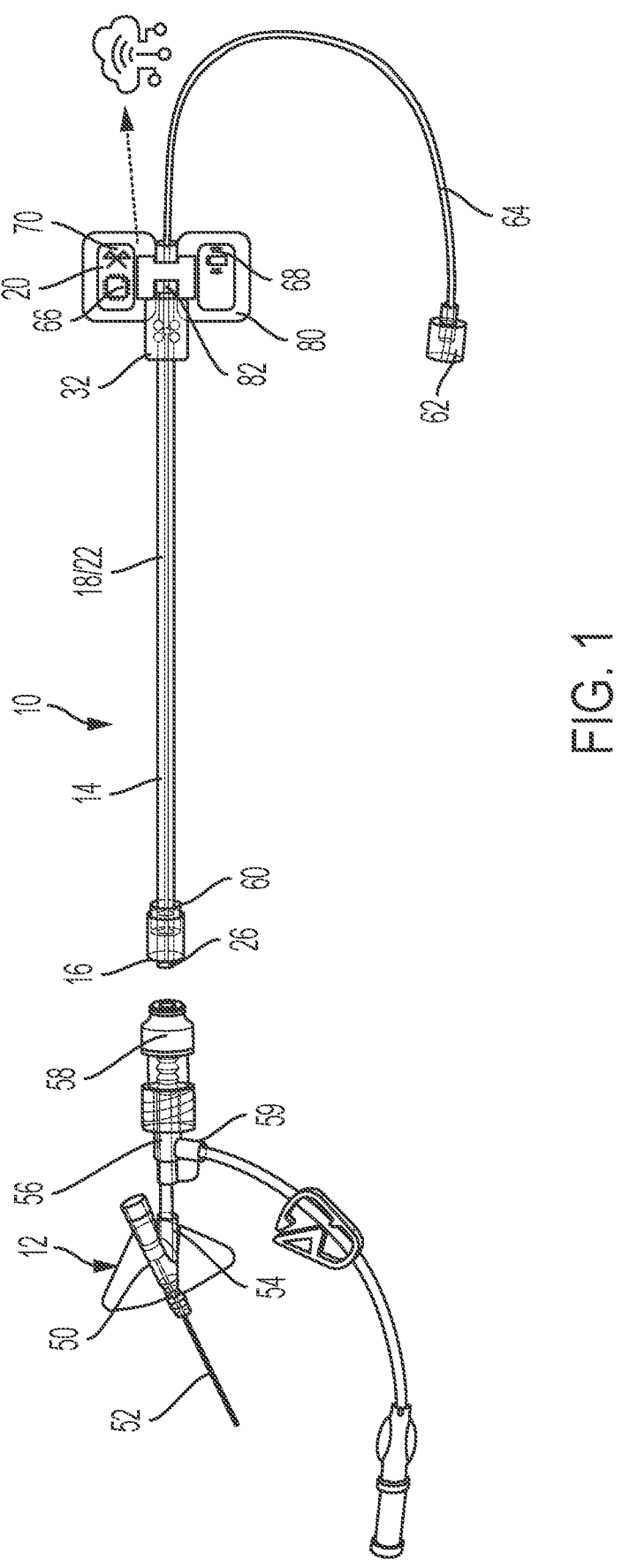
FIG. 1 is a top view of a sensor deployment system for a vascular access device according to one aspect or embodiment of the present application, showing the system uncoupled from the vascular access device.
Figure 2:
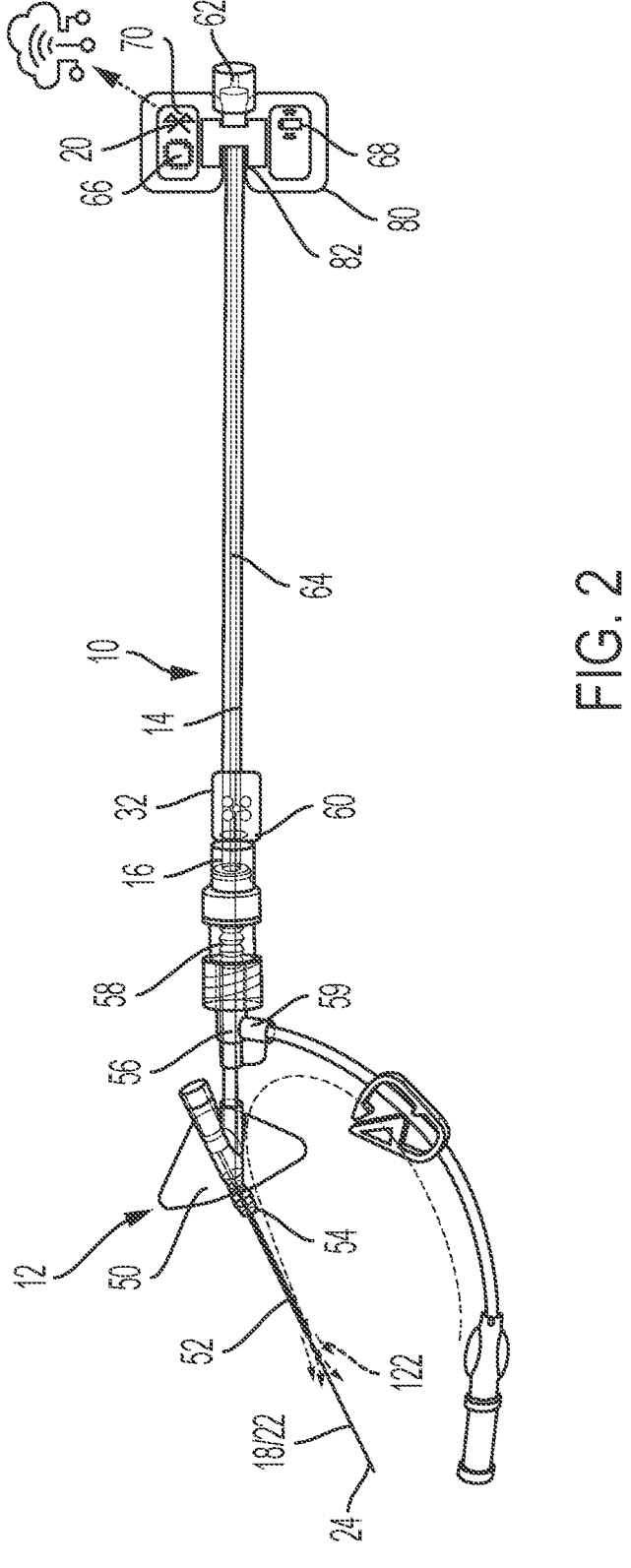
FIG. 2 is a top view of the sensor deployment system of FIG. 1, showing the system coupled to the vascular access device and in an advanced position.
Figure 4:
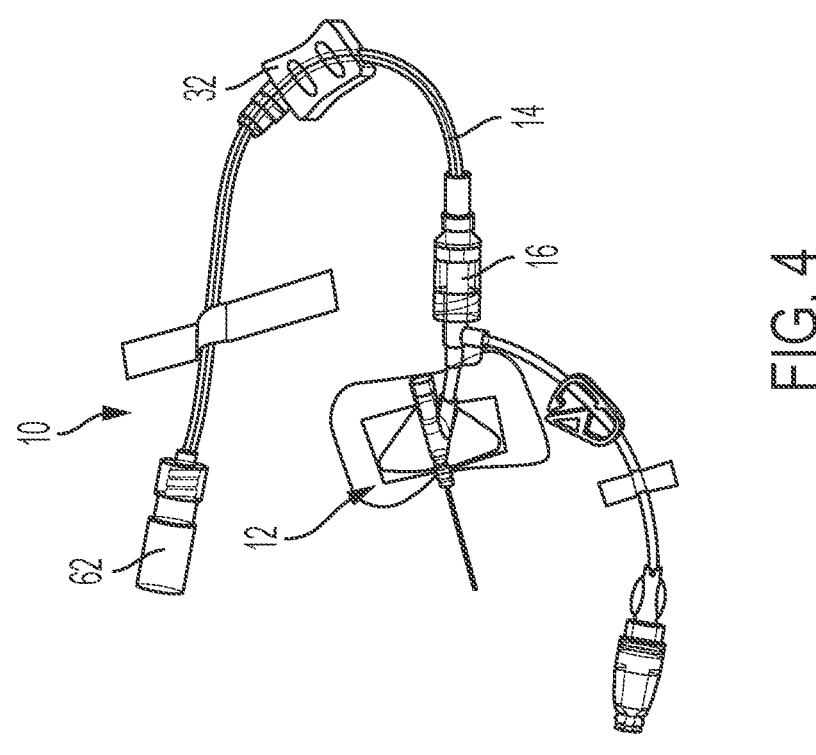
FIG. 4 is a top view of the sensor deployment system of FIG. 3, showing the system coupled to the vascular access device.
Figure 3:
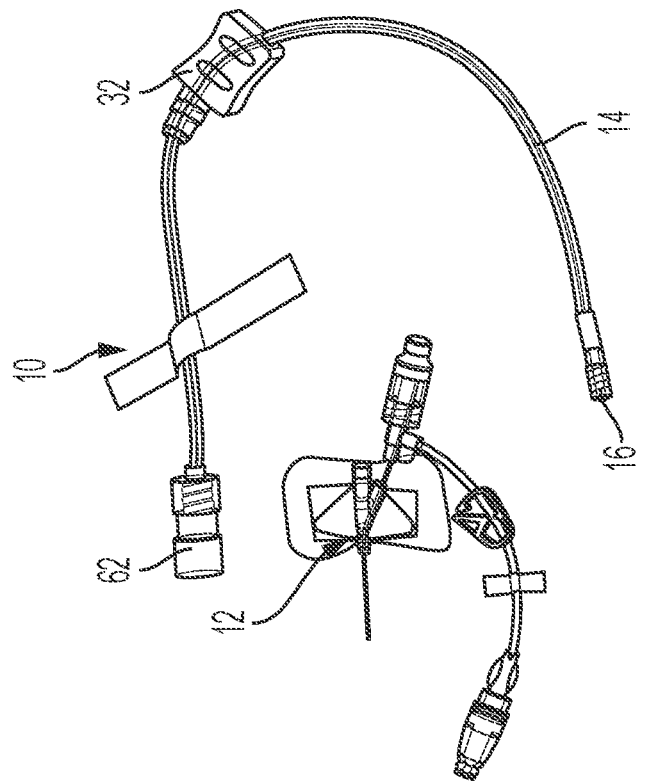
FIG. 3 is a top view of a sensor deployment system for a vascular access device according to a further aspect or embodiment of the present application, showing the system uncoupled from the vascular access device.
Figure 5:
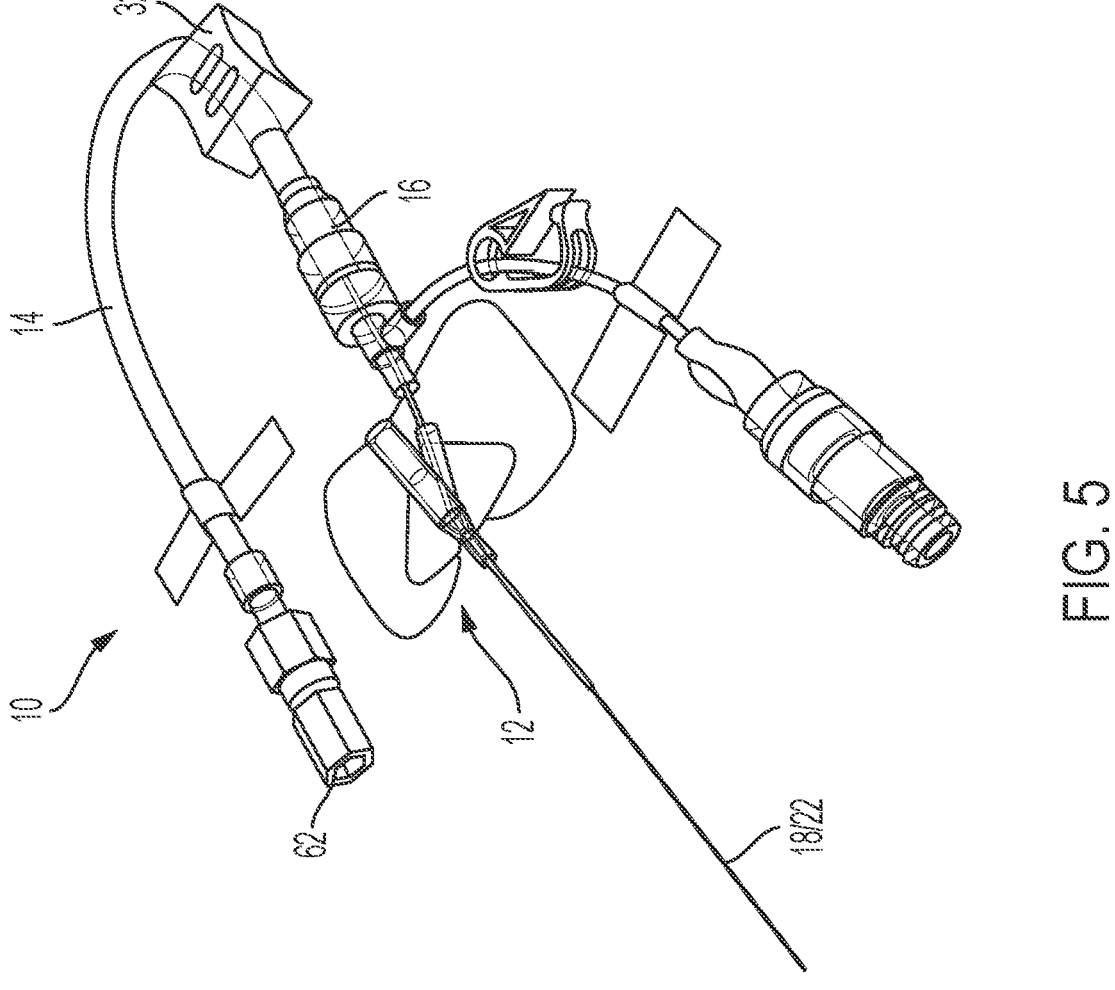
FIG. 5 is a perspective view of the sensor deployment system of FIG. 3, showing the system coupled to the vascular access device.
Figure 6:
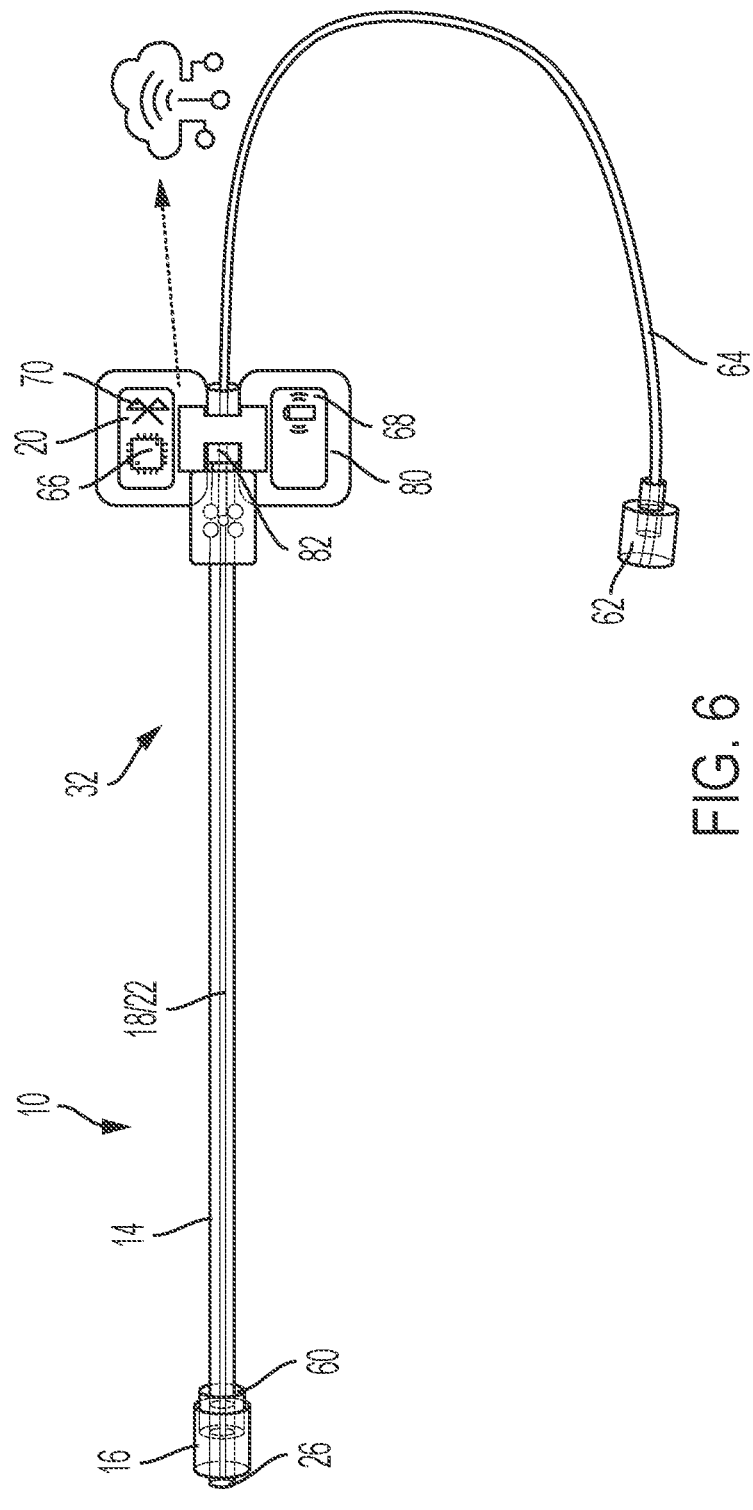
FIG. 6 is a top view of the sensor deployment system of FIG. 1.
Figure 7:
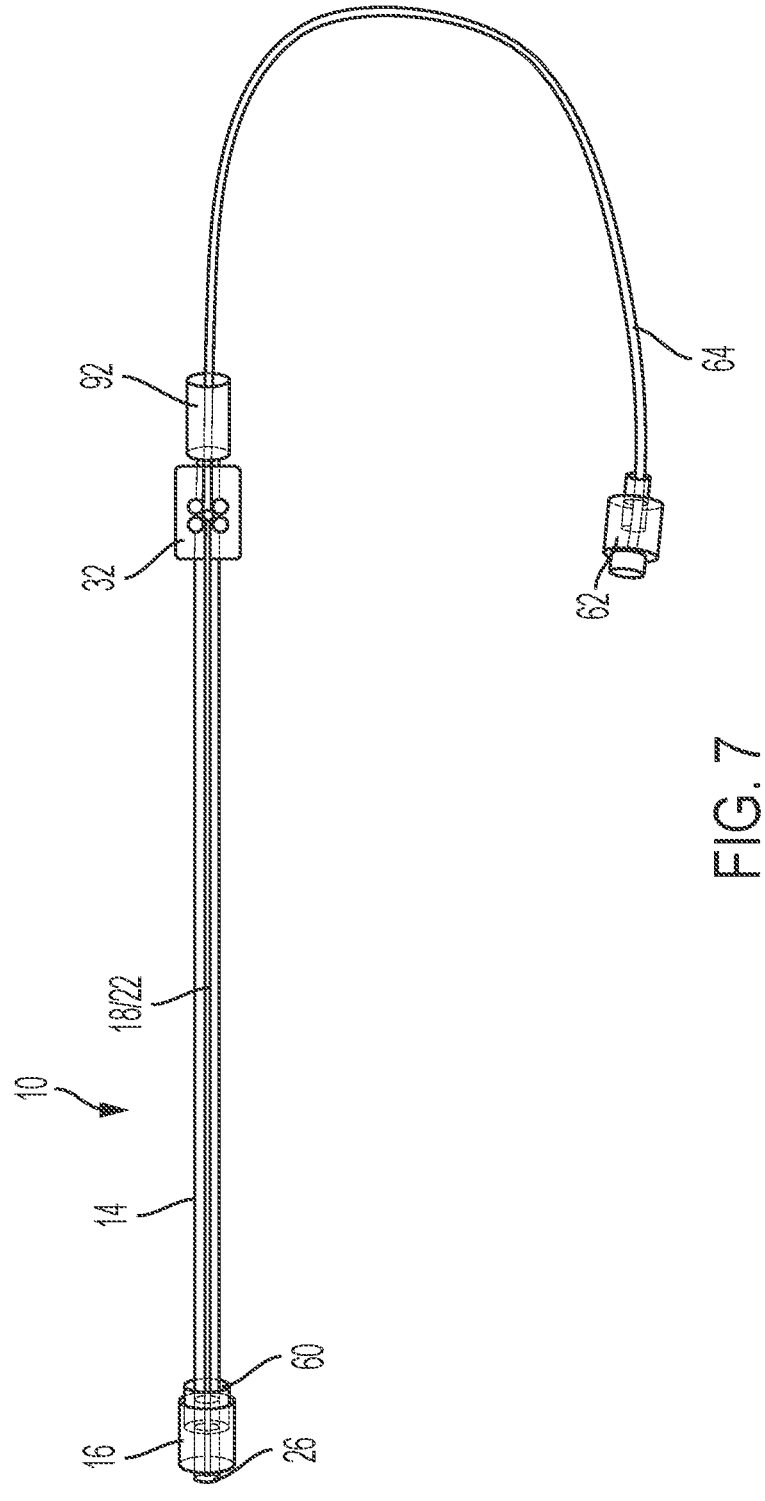
FIG. 7 is a top view of a sensor deployment system according to a further aspect or embodiment of the present application.

Spatial or directional terms, such as "left", "right", "inner", "outer", "above", "below", and the like, are not to be considered as limiting as the invention can assume various alternative orientations.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less.

The terms "first", "second", and the like are not intended to refer to any particular order or chronology, but refer to different conditions, properties, or elements.

As used herein, "at least one of" is synonymous with "one or more of". For example, the phrase "at least one of A, B, and C" means any one of A, B, or C, or any combination of any two or more of A, B, or C. For example, "at least one of A, B, and C" includes one or more of A alone; or one or more of B alone; or one or more of C alone; or one or more of A and one or more of B; or one or more of A and one or more of C; or one or more of B and one or more of C; or one or more of all of A, B, and C.

Referring to FIGS. 1-6, in one aspect or embodiment, a sensor deployment system 10 for a vascular access device 12 includes a primary lumen 14, a deployment connector 16, an instrument 18 at least partially received within the primary lumen 14, and a communication device 20. The deployment connector 16 is configured to be connected to at least one of a luer connector, a needle-free connector, and a catheter adapter, with the deployment connector 16 attached to the primary lumen 14. The instrument 18 includes a sensor 22. The instrument 18 has a retracted position (FIG. 1) where a distal end 24 of the instrument 18 is positioned within the primary lumen 14 or deployment connector 16 and an extended position (FIG. 2) where the distal end 24 of the instrument 18 extends beyond a distal end 26 of the primary lumen 14 and the deployment connector 16. The communication device 20 is configured to transmit data from the sensor 22. The sensor deployment system 10 is configured to provide closed system instrument access to a patient's vascular system for venous, arterial, or fluid path data capture throughout the dwell time of the vascular access device 12 for short or long-term sensing and data capture. Further, the sensor deployment system 10 is configured to provide support, alignment, and aseptic delivery of the instrument 18 and the sensor 22 through the vascular access device 12 and into the patient's vascular system. The instrument 18 is flexible to facilitate introduction of the sensor 22 into the patient's vasculature. The sensor deployment system 10 is configured to be compatible with existing and emerging vascular access devices and is configured to be scaled for use with peripheral intravenous catheters, midlines, peripherally inserted central catheters, and central venous catheters for in-vein sensing via peripheral, internal jugular, femoral, central venous, and/or arterial access. Continuous real-time in-vein measurement of patient parameters may provide early indications of emerging disease states, such as sepsis, or indications of efficacy of therapeutic treatment.

In some aspects or embodiments, the primary lumen 14 is flexible and may be formed from extension tubing. The primary lumen 14 may be formed from TPE, TPU, PVC, or other suitable tubing material. Additives may be provided in connection with the primary lumen 14 to increase lubricity. The primary lumen 14 may be flexible, semi-rigid, or rigid. The primary lumen 14 may include markers or other indicia to inform a healthcare clinician the position of the instrument 18 relative to the vascular access device 12. The primary lumen 14 may be transparent or opaque. The primary lumen 14 may include a textured surface to reduce contact friction. The primary lumen 14 may be non-vented or vented (open air pathway, breathable filter membrane, porous venting material, micro-channels, etc.).

In some aspects or embodiments, the sensor 22 includes at least one of a temperature sensor, a pressure sensor, a pH sensor, a flow rate sensor, and an optical sensor. In one aspect or embodiment, the sensor 22 is a lactate sensor. In one aspect or embodiment, the sensor 22 monitors core body temperature or pressure via vascular access in the internal jugular. The sensor(s) 22 may measure at least one of blood flow rate, temperature-based cardiac output, fluid path system pressure, heart rate, blood gasses, and SpO2 levels and other physiological parameters. Absolute or trending of body temperature may be used to provide an indication of changes to the patient's condition or response to therapy or treatment. The sensor(s) 22 may be near the distal end of the instrument 18, along a length of the instrument 18, and/or positioned to facilitate measuring multiple parameters. For example, the sensor(s) 22 deployed within a vein may measure temperature and flow rate, while the sensor(s) located elsewhere may measure pressure. The communication device 20, as discussed in more detail below, may transmit data, via a wired connection or wirelessly, to a local hub, the cloud, a nurse monitoring station, and/or electronic medical record.

Figure 22:
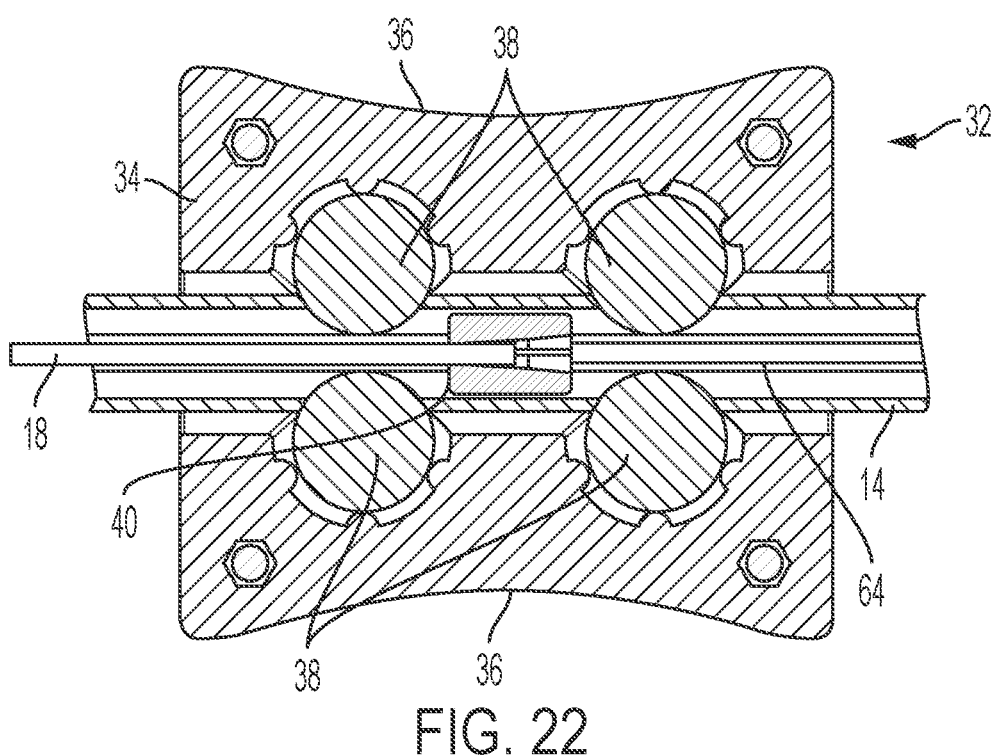
FIG. 22 is a cross-sectional view of an advancement mechanism according to one aspect or embodiment of the present application.
Figure 23:
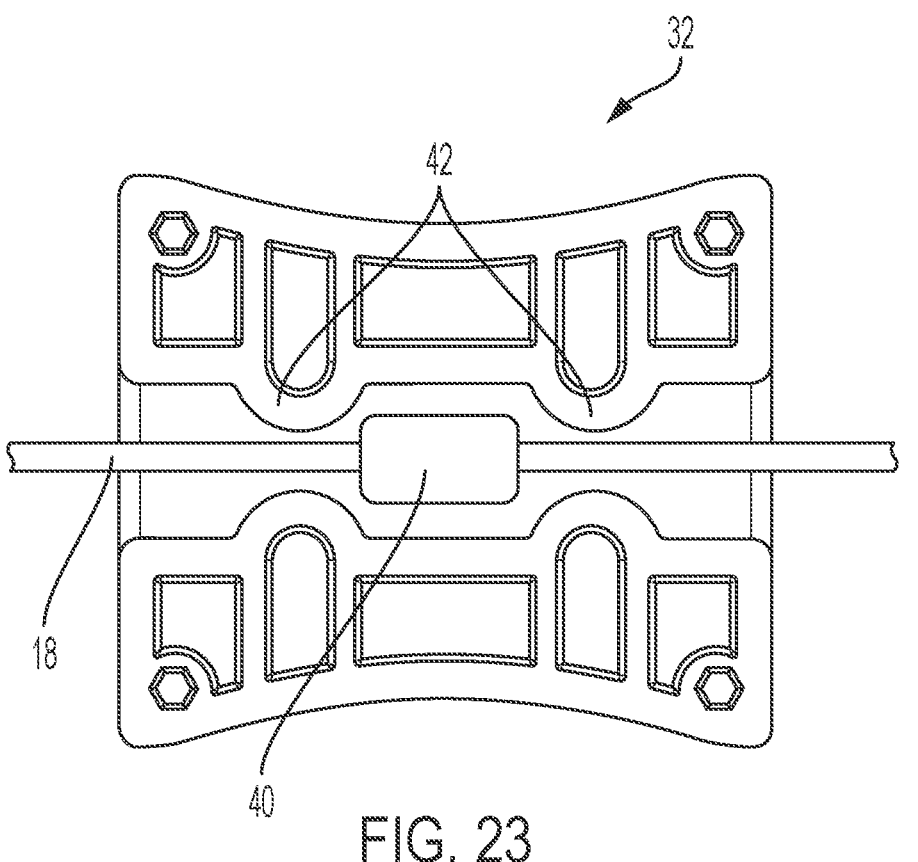
FIG. 23 is a cross-sectional view of an advancement mechanism according to a further aspect or embodiment of the present application.

Referring to FIGS. 1-6, 22, and 23, the sensor deployment system 10 includes an advancement member 32 configured to be grasped by a healthcare technician, where movement of the advancement member 32 moves the instrument 18 between the retracted position and the extended position. The advancement member 32 is configured to move along an outer surface of the primary lumen 14, with the advancement member 32 entirely positioned outside of the primary lumen 14. As shown in FIG. 22, the advancement member 32 includes a body 34 having gripping surfaces 36 and ball bearings 38 that engage the outer surface of the primary lumen 14. A coupler 40 is positioned within the primary lumen 14, with the instrument 18 attached to the coupler 40. The coupler 40 is positioned between the ball bearings 38. In one aspect or embodiment, as shown in FIG. 23, rather than providing the ball bearings 38, the body 34 of the advancement member may include bumps 42, such as cylindrical or spherical bumps, that engage the outer surface of the primary lumen 14. Movement of the advancement member 32 distally or proximally causes the ball bearings 38 to engage the coupler 40, with the primary lumen 14 depressed and positioned between the ball bearings 38 and the coupler 40, thereby moving the coupler 40 and the instrument 18 along with the advancement member 32. The advancement member 32 may be the same or similar to the translation handle shown and described in U.S. Patent Application Publication No. 2021/0290126, which is hereby incorporated by reference in its entirety. The advancement member 32 may include lubrication around the coupler 40 and/or around the bumps 42 or bearings 38. The instrument 18 may also include one or more support features configured to ease insertion of the instrument 18 using the advancement member 23 by minimizing bowing of the instrument 18 during insertion.

Referring again to FIGS. 1-6, in some aspects or embodiments, the vascular access device 12 includes a catheter adapter 50 having a catheter 52 configured to be inserted into a patient's vasculature, with the deployment connector 16 configured to be connected to the catheter adapter 50. The catheter adapter 50 includes a side port 54 and a joining connector 56 in fluid communication with the side port 54. The deployment connector 16 is configured to be connected to the joining connector 56. The joining connector 56 may include a near patient access port or needle-less connector 58 for connection to the deployment connector 16. With multiple access points, fluid and medication delivery can continue, as needed, through an additional port 59 of the joining connector 56. The deployment connector 16 includes an instrument seal 60 configured to maintain a seal between the primary lumen 14 and the instrument 18 at the distal end 26 of the primary lumen 14. Accordingly, a portion of the deployment connector 16 is configured to be within a fluid path of the vascular access device 12, with the instrument seal 60 sealing the primary lumen 14 from the fluid path of the vascular access device 12. In some aspects or embodiments, the instrument 18 includes a nitinol guidewire with an atraumatic tip. In some aspects or embodiments, the instrument 18 is extruded tubing containing sensor wiring and/or combined nitinol wire and tubing assembly. In some aspects or embodiments, the sensor deployment system 10 includes an electrical connector 62 and wiring 64 in communication with the sensor(s) 22. The wiring 64, such as insulated wiring, may be connected to the coupler 40 of the advancement member 32. The communication device 20 includes a processor 66, a power source 68, and a radio transceiver 70. In some aspects or embodiments, the sensor(s) 22 are connected to a battery-powered data reader, processor, signal conditional device, visual indicator, and/or wireless radio transceiver that may communicate with an external device, monitor, and/or the cloud.

Referring to FIGS. 1-5, the sensor deployment system 10 includes a stabilization member 80 configured to be in contact with a patient's skin, with the communication device 20, the processor 66, and the power source 68 received by the stabilization member 80. In some aspects or embodiments, the communication device 20 is integrated within the stabilization member 80. The stabilization member 80 is configured to provide a reliable way of securing the sensor deployment device 10 in the desired location on the patient for longer term sensing. The stabilization member 80 may be positioned at a proximal end 82 of the primary lumen 14, although other suitable positions and configurations may be utilized. In some aspects or embodiments, as in FIGS. 3-5 and 7, the sensor deployment system 10 does not include the stabilization member 80, with the electrical connector 62 providing a wired only connection to the sensor(s) 22.

Figure 8:
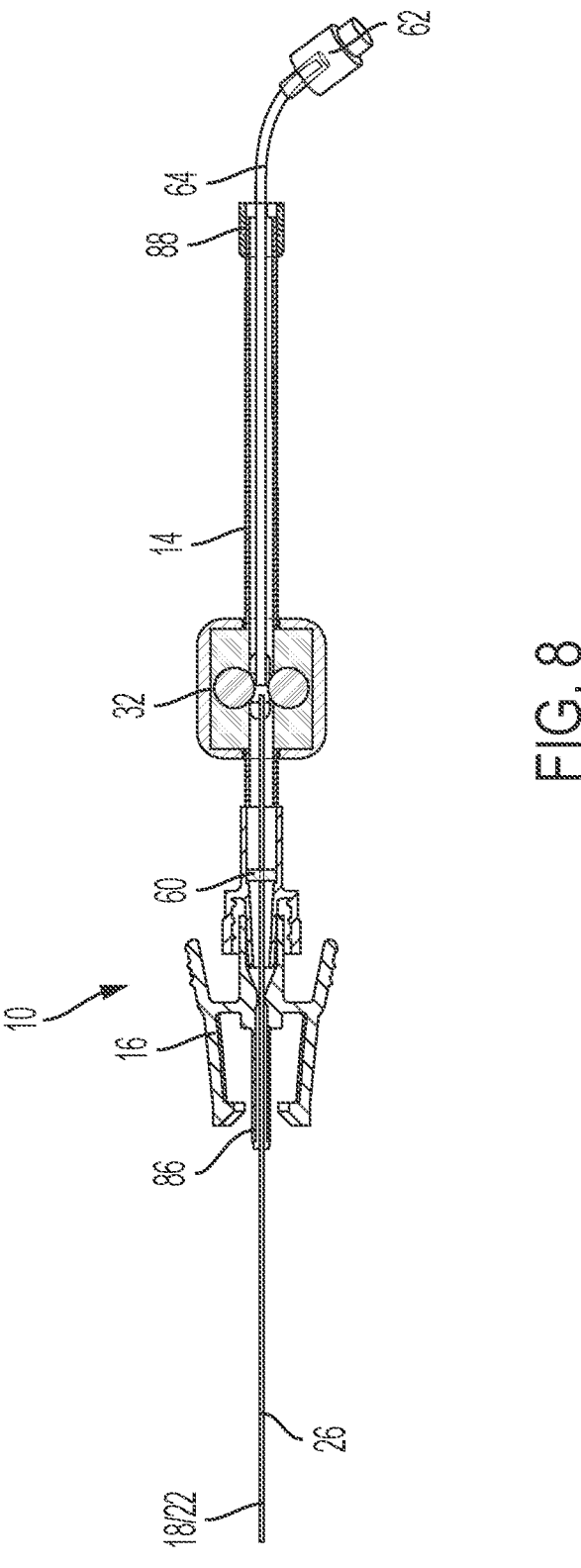
FIG. 8 is a partial cross-sectional view of a sensor deployment system according to a further aspect or embodiment of the present application.
Figure 11:
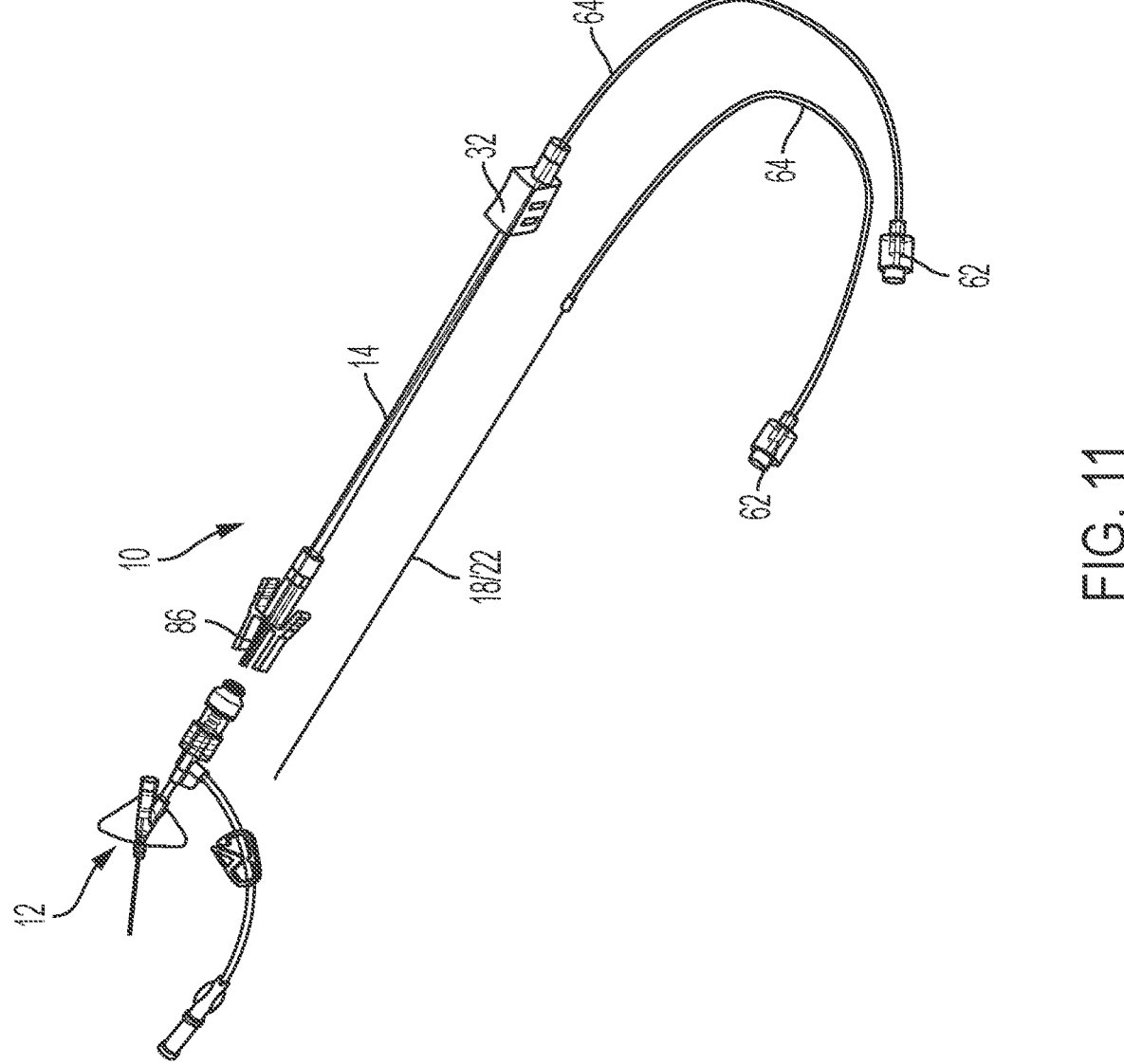
FIG. 11 is a perspective view of the sensor deployment system of FIG. 1, showing an instrument alongside of the system.

Referring to FIGS. 8 and 11, in some aspects or embodiments, the deployment connector 16 includes a blunt cannula 86 configured to be inserted into a needle-free connector. The primary lumen 14 may also include a proximal bushing and grip 88, with the wiring 64 extending through the bushing 88.

Figures 9, 10:
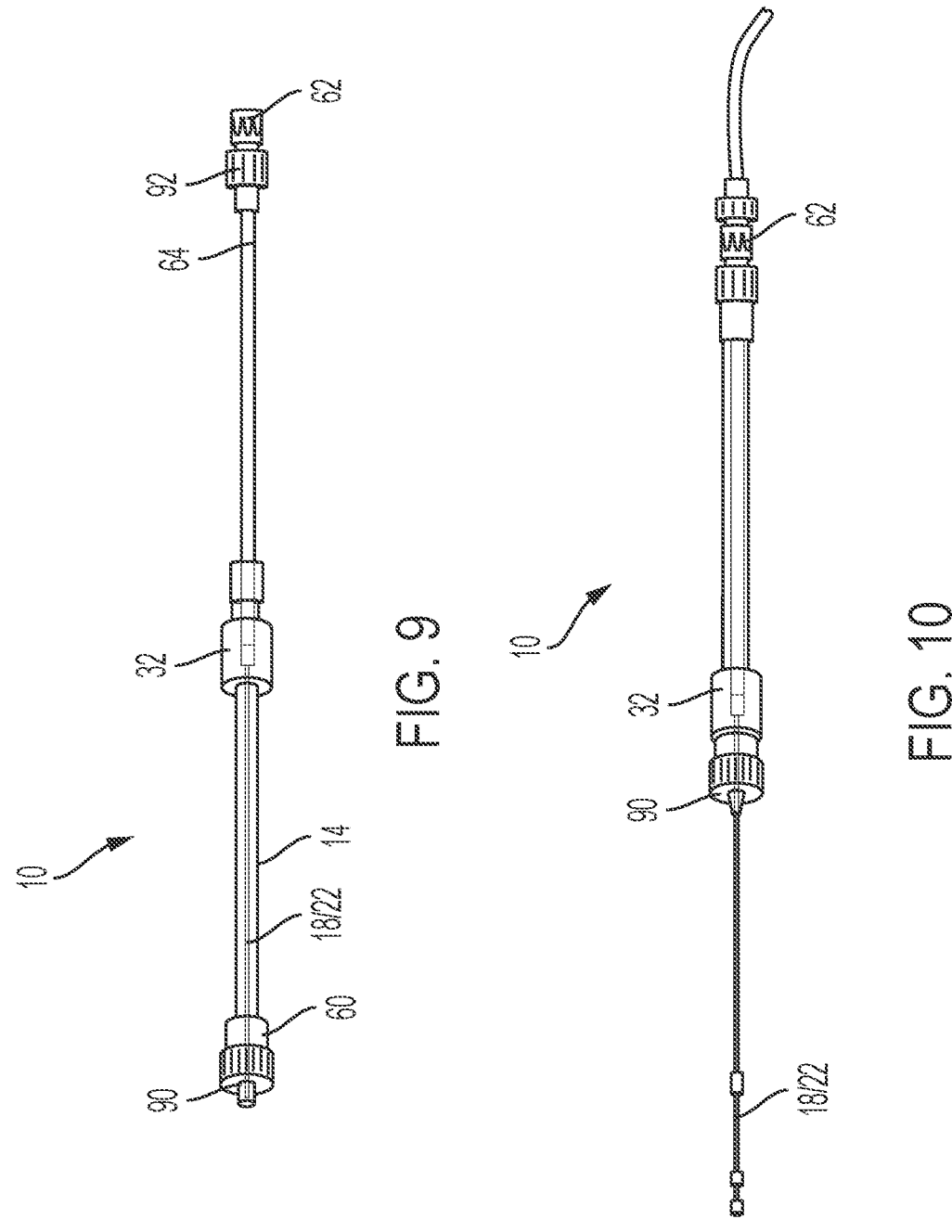
FIG. 9 is a perspective view of a sensor deployment system according to a further aspect or embodiment of the present application, showing a retracted position of the system.
FIG. 10 is a perspective view of the sensor deployment system of FIG. 9, showing an advanced position of the system.

Referring to FIGS. 9 and 10, in some aspects or embodiments, the deployment connector 16 includes a threaded luer connector 90 positioned at the distal end 26 of the primary lumen 14.

Figure 12:
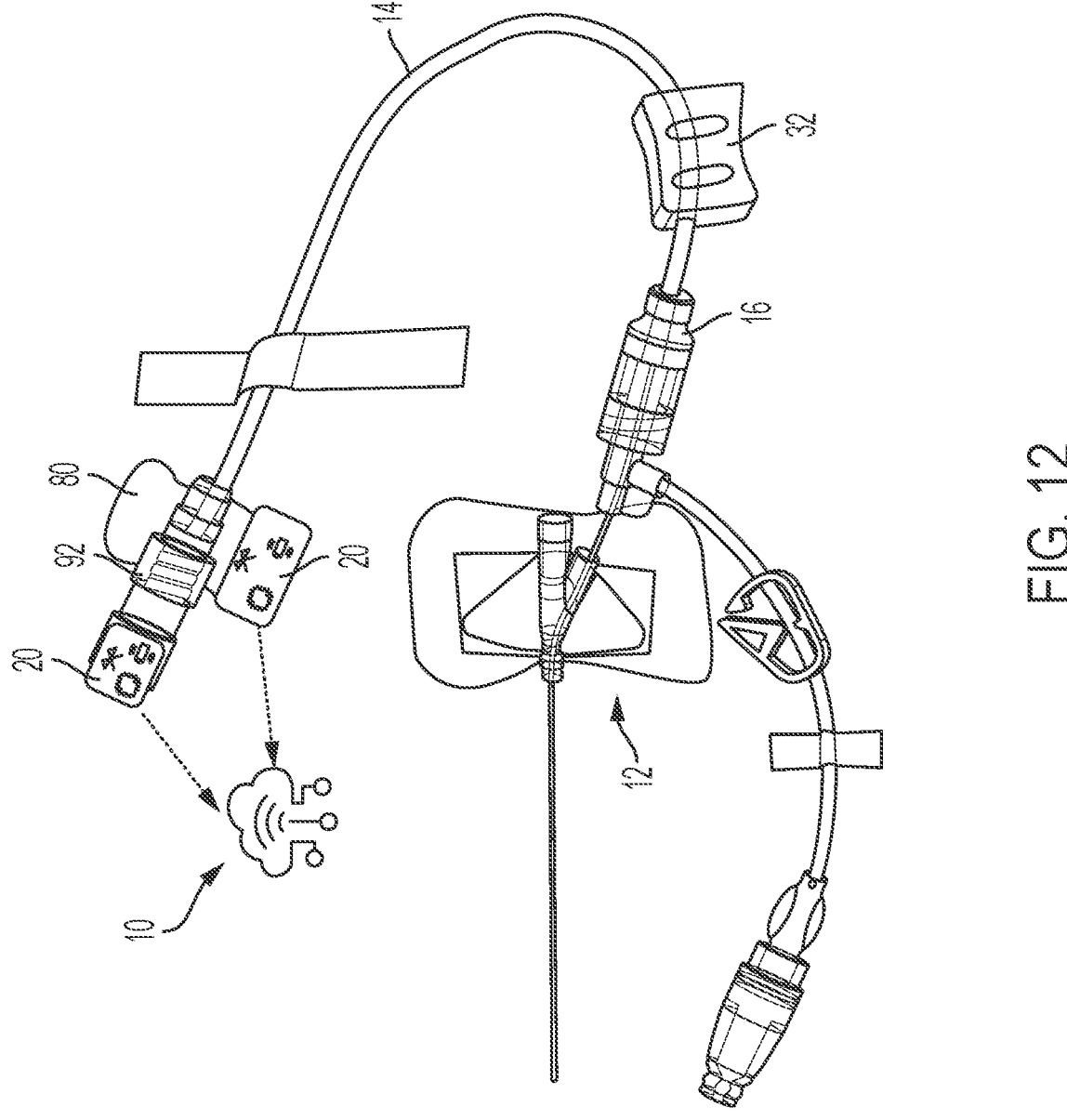
FIG. 12 is a top view of a sensor deployment system for a vascular access device according to a further aspect or embodiment of the present application, showing an advanced position of the system.

Referring to FIG. 12, in some aspects or embodiments, the communication device 20 is positioned at the proximal end 82 of the primary lumen 14. The communication device 20 may be incorporated into the stabilizer 80, or separately attached or integrated into a proximal connector 92 or the electrical connector 62.

Figure 13:
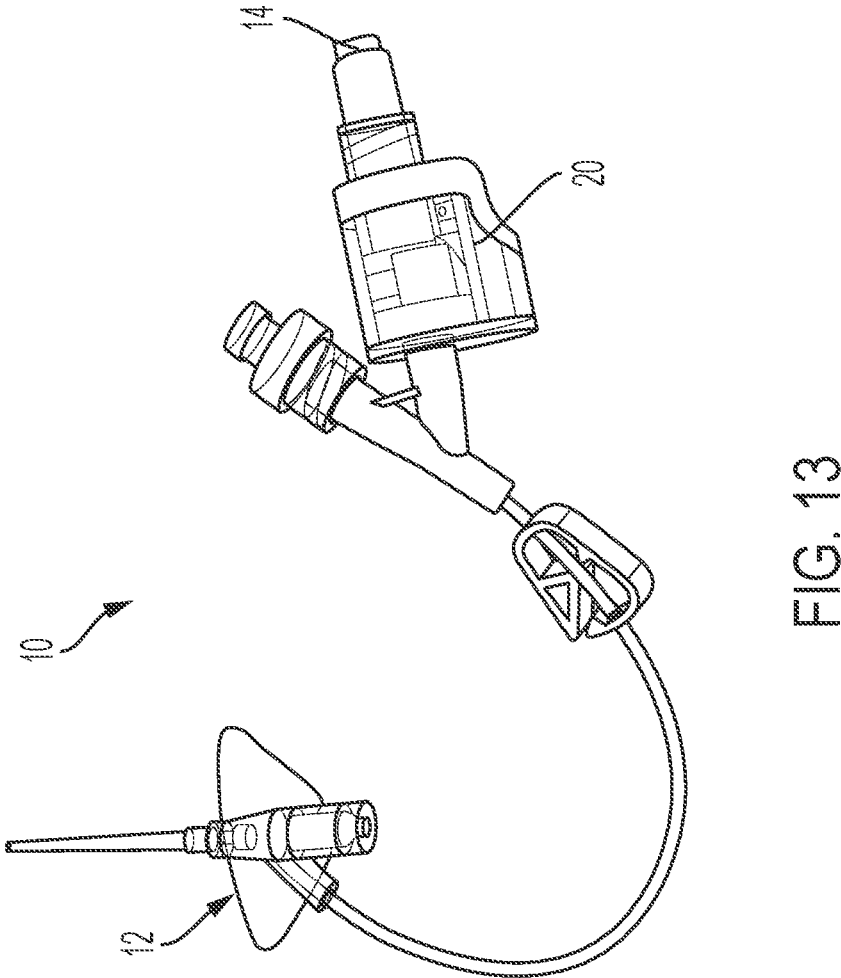
FIG. 13 is a partial top view of a sensor deployment system for a vascular access device according to a further aspect or embodiment of the present application.

Referring to FIG. 13, in some aspects or embodiments, the communication device 20 is positioned at the distal end 26 of the primary lumen 14.

Figure 14:
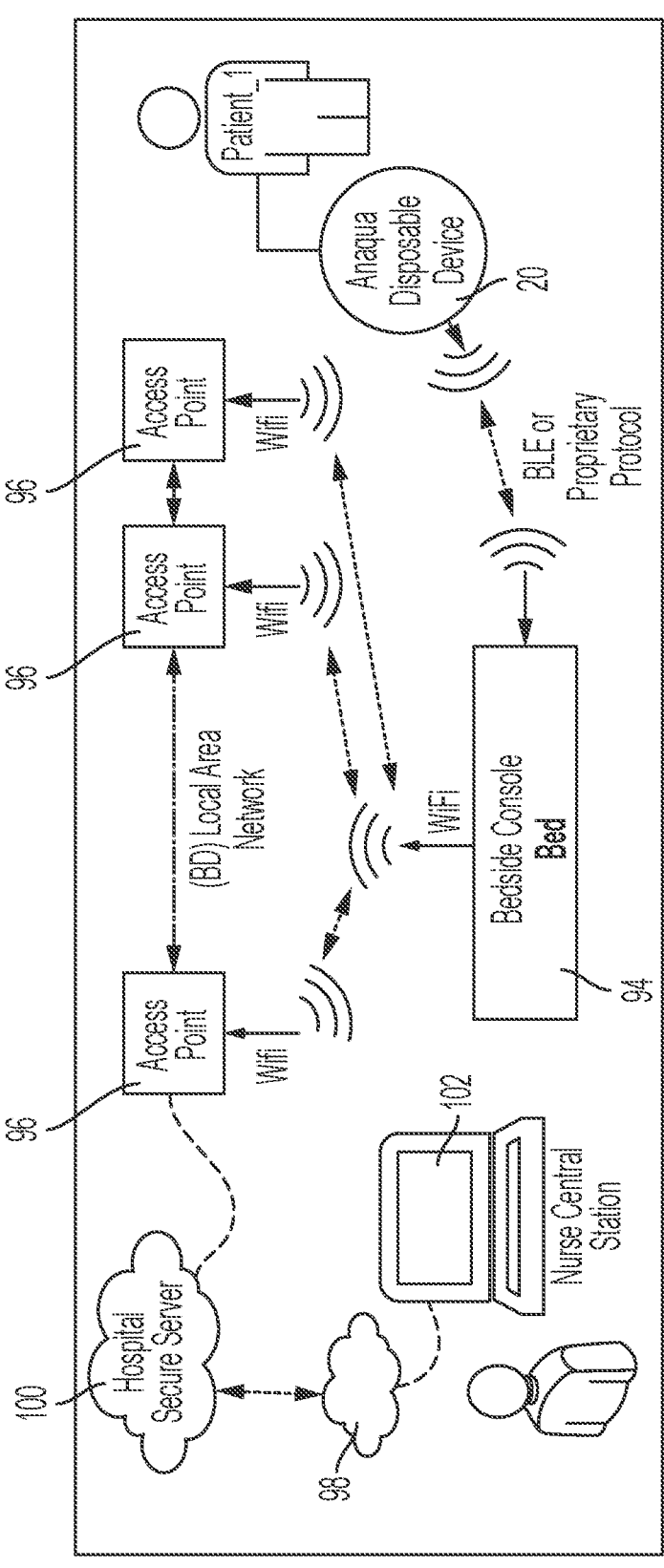
FIG. 14 is a schematic view of a data capture and communication system according to one aspect or embodiment of the present application.
Figure 15:
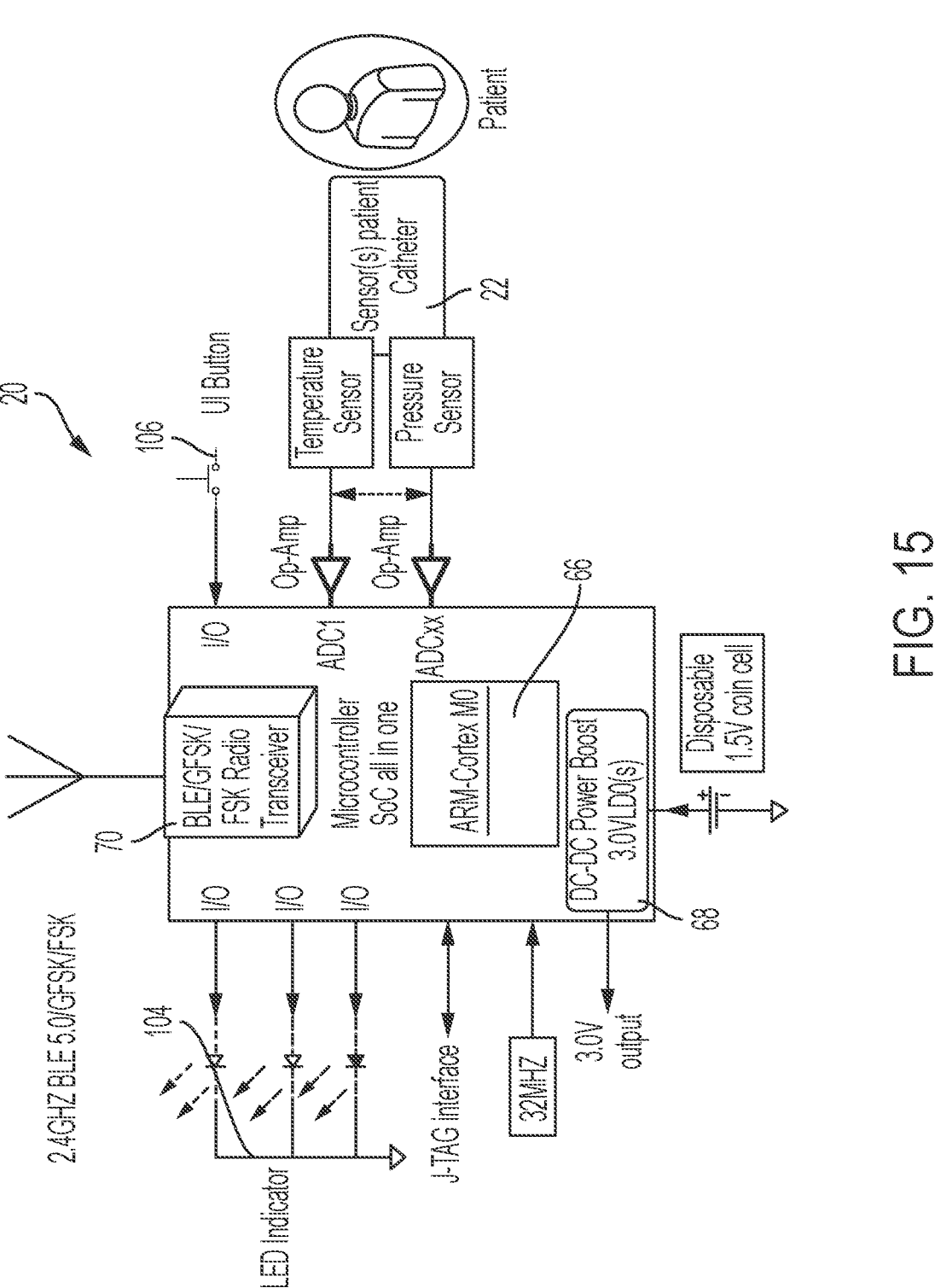
FIG. 15 is a schematic view of the data capture system of FIG. 14.
Figure 16:
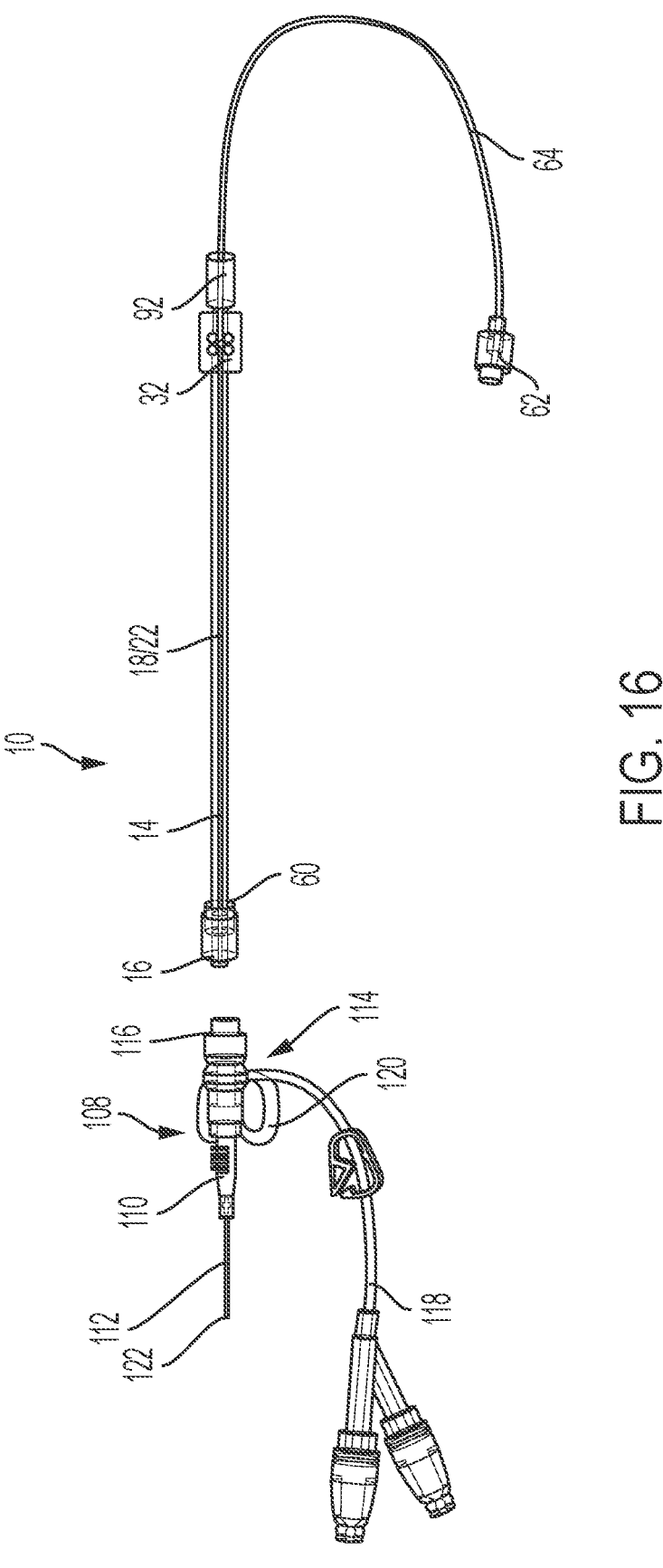
FIG. 16 is a top view of a sensor deployment system for a vascular access device according to a further aspect or embodiment of the present application, showing the system uncoupled from the vascular access device.

Referring to FIGS. 14 and 15, the communication device 20 is configured to transmit data from the sensor(s) 22 wirelessly, such as through a Bluetooth connection, or through a wired connection to various external devices. In one aspect or embodiment, the communication device 20 transmits data from the sensor(s) 22 to a bedside console 94, which, in turn, transmits the data to a local area network via WiFi access points 96 or another suitable network connection. The local area network may be connected the cloud 98 and/or secure hospital server 100, which can be accessed at a nurse central station 102 or other remote location. The processor 66, the radio transceiver 70, a light or other indicators 104 of the communication device 20 may be provided on a SoC microcontroller, although other suitable configurations may be utilized. The communication device 20 may include a user interface 106 having a display, button, or other suitable features.

Figure 17:
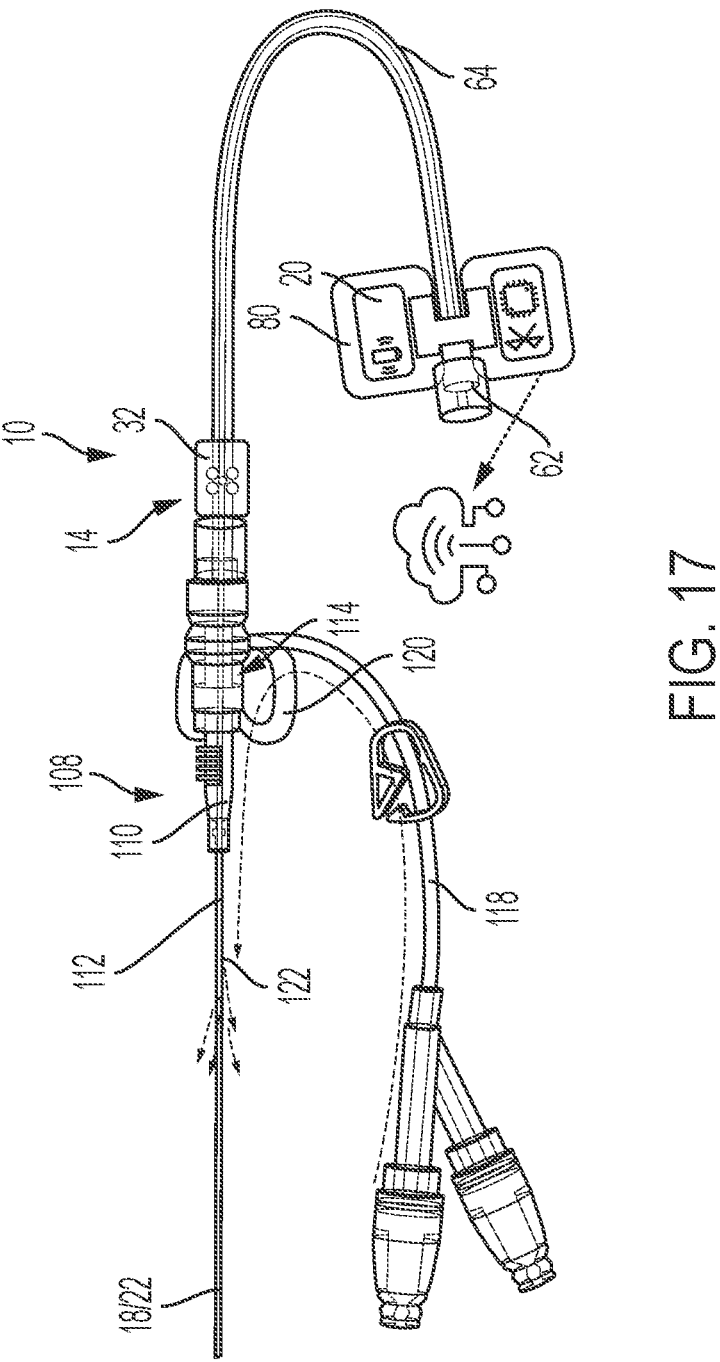
FIG. 17 is a top view of the sensor deployment system of FIG. 16, showing the system coupled to the vascular access device and in an advanced position.
Figure 18:
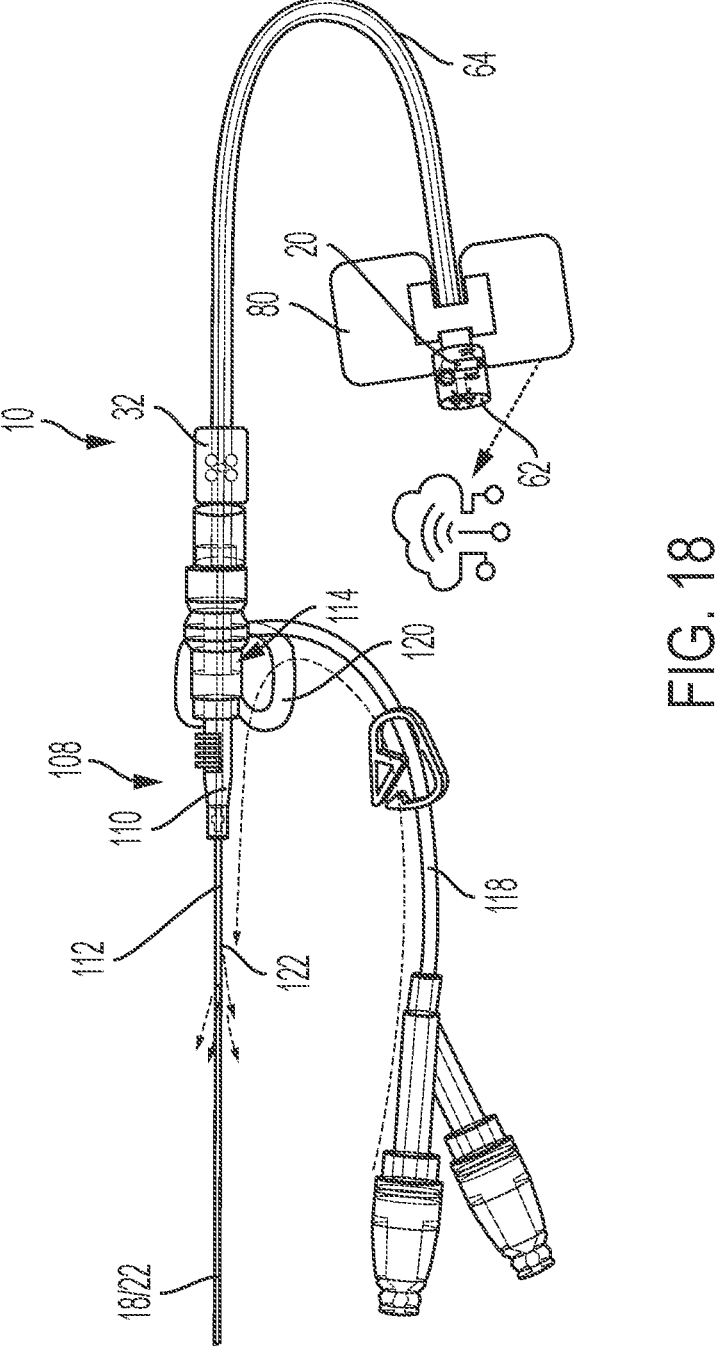
FIG. 18 is a top view of the sensor deployment system of FIG. 16, showing the system coupled to the vascular access device and in an advanced position and with an integrated power source.
Figures 19, 20, 21:
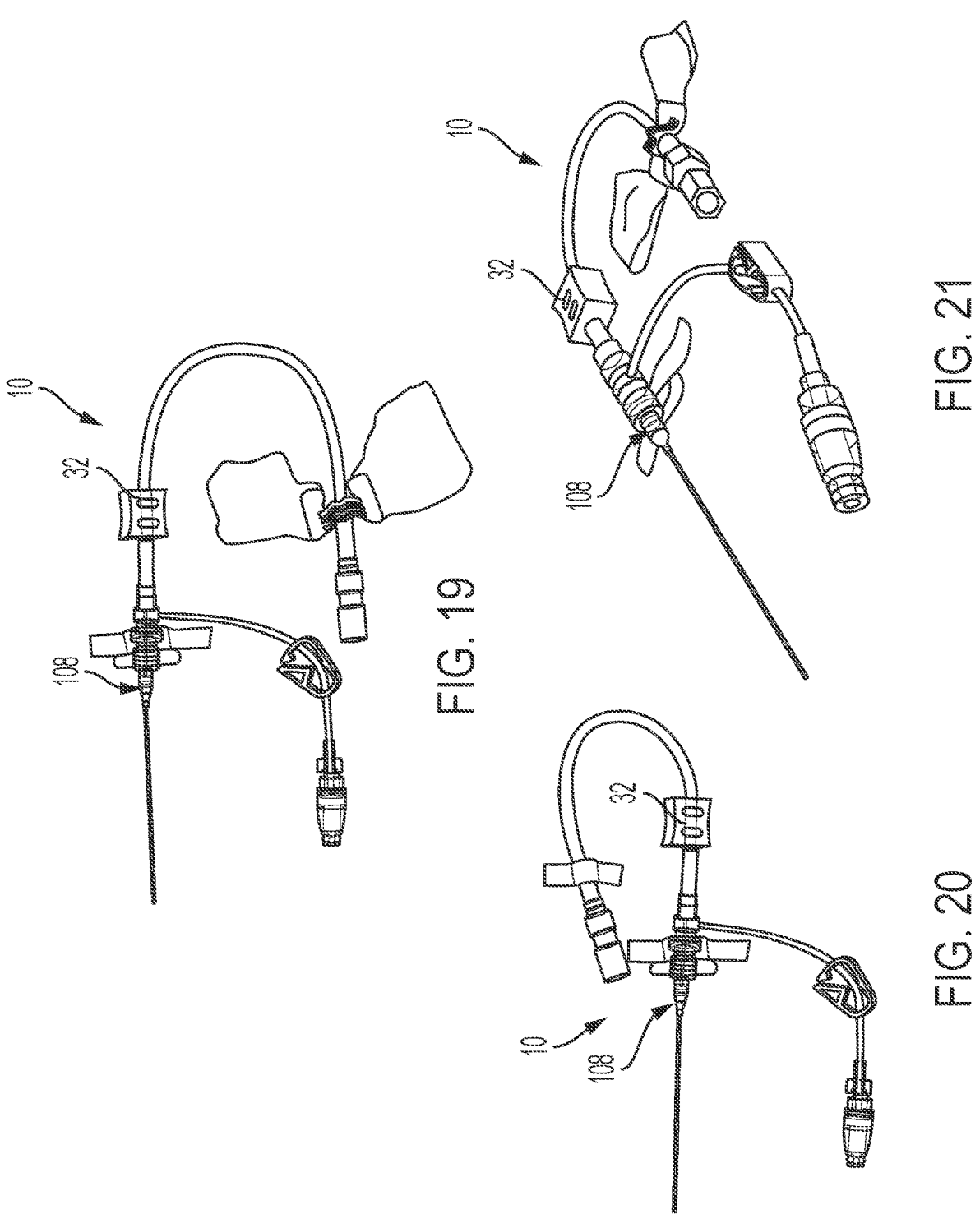
FIG. 19 is a top view of a sensor deployment system for a vascular access device according to a further aspect or embodiment of the present application, showing an advanced position of the system.
FIG. 20 is a top view of the sensor deployment system of FIG. 19, showing the system without a stabilization device.
FIG. 21 is a perspective view of the sensor deployment system of FIG. 19.

Referring to FIGS. 16-21, in some aspects or embodiments, the sensor deployment system includes or is configured to be utilized with a non-integrated catheter 108. The non-integrated catheter 108 includes a catheter adapter 110 having a catheter 112 configured to be inserted into a patient's vasculature and an extension set 114 having a near patient access port 116 and an extension tube 118 in fluid communication with the near patient access port 116. The deployment connector 16 is configured to be connected to the near patient access port 116. The extension set 114 includes an extension set stabilization member 120 configured to contact a patients' skin. As shown in FIGS. 17 and 18, for example, the sensor deployment system 10 may include the stabilization member 80 positioned at the proximal end 82 of the primary lumen 14, with the communication device 20 received by the stabilization member 80 (FIG. 17) or integrated into the electrical connector 62 (FIG. 18). In one aspect or embodiment, the extension set 114 is the same or similar to one of the extension sets shown and described in U.S. Pat. No. 11,191,939, which is hereby incorporated by reference in its entirety. As shown in FIGS. 19-21, in some aspects or embodiments, the primary lumen 14 is flexible, which is configured to improve securement of the sensor deployment system 10 on a patient for short or long term in-vein sensing.

In one aspect or embodiment, the sensor deployment system 10 may be used by: connecting the deployment connector 16 to the catheter adapter 50, 110 having the catheter 52, 112; advancing the instrument 18 from the retracted position to the extended position such that the distal end 24 of the instrument 18 extends beyond a distal end 122 of the catheter 52, 112; collecting data from the sensor(s) 22; and transmitting the data to an external device, such as an electronic medical record, bedside console 94, access point 96, cloud 98, or server 100, using the communication device 20.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A sensor deployment system for a vascular access device, the system comprising:
a primary lumen;
a deployment connector configured to be connected to at least one of a luer connector, a needle-free connector, and a catheter adapter, the deployment connector attached to the primary lumen;
an instrument at least partially received within the primary lumen, the instrument comprising a sensor, the instrument having a retracted position where a distal end of the instrument is positioned within the primary lumen or the deployment connector and an extended position where the distal end of the instrument extends beyond a distal end of the primary lumen and the deployment connector;
a communication device configured to transmit data from the sensor; and
an advancement member configured to be grasped by a healthcare technician, wherein movement of the advancement member moves the instrument between the retracted position and the extended position, wherein the advancement member is configured to move along an outer surface of the primary lumen, and wherein the advancement member is entirely positioned outside of the primary lumen.

2. The sensor deployment system of claim 1, further comprising a catheter adapter comprising a catheter configured to be inserted into a patient's vasculature, the deployment connector configured to be connected to the catheter adapter.

3. The sensor deployment system of claim 2, wherein the catheter adapter comprises a side port and a joining connector in fluid communication with the side port, and wherein the deployment connector is configured to be connected to the joining connector.

4. The sensor deployment system of claim 3, wherein the joining connector comprises a needle-free connector, and wherein the deployment connector comprises a blunt cannula.

5. The sensor deployment system of claim 1, wherein the deployment connector comprises an instrument seal.

6. The sensor deployment system of claim 1, wherein the instrument comprises a nitinol guidewire with an atraumatic tip.

7. The sensor deployment system of claim 1, further comprising an electrical connector and wiring in communication with the sensor.

8. The sensor deployment system of claim 1, wherein the communication device comprises a processor and a power source.

9. The sensor deployment system of claim 8, wherein the communication device comprises a radio transceiver.

10. The sensor deployment system of claim 8, further comprising a stabilization member configured to be in contact with a patient's skin, wherein the communication device, the processor, and the power source are received by the stabilization member.

11. The sensor deployment system of claim 10, wherein the stabilization member is positioned at a proximal end of the primary lumen.

12. The sensor deployment system of claim 8, wherein the communication device is positioned at the distal end of the primary lumen.

13. The sensor deployment system of claim 1, wherein the sensor comprises at least one of a temperature sensor, a pressure sensor, a pH sensor, a flow rate sensor, and an optical sensor.

14. The sensor deployment system of claim 1, wherein the deployment connector comprises a threaded luer connector positioned at the distal end of the primary lumen.

15. The sensor deployment system of claim 1, further comprising a catheter adapter comprising a catheter configured to be inserted into a patient's vasculature and an extension set comprising a near patient access port and an extension tube in fluid communication with the near patient access port, wherein the deployment connector is configured to be connected to the near patient access port.

16. The sensor deployment system of claim 15, wherein the extension set comprises an extension set stabilization member configured to contact a patient's skin.

17. The sensor deployment system of claim 15, further comprising a stabilization member configured to be in contact with a patient's skin, the stabilization member positioned at a proximal end of the primary lumen, wherein the communication device comprises a processor and a power source, and wherein the communication device is received by the stabilization member.

18. The sensor deployment system of claim 15, wherein the communication device comprises a processor and a power source, and wherein the communication device is positioned at a proximal end of the primary lumen.

* * * * *